US009072785B2

(12) United States Patent
Zhu et al.

(10) Patent No.: US 9,072,785 B2
(45) Date of Patent: Jul. 7, 2015

(54) STABILIZED COMPOSITIONS OF PROTEINS HAVING A FREE THIOL MOIETY

(71) Applicant: SHIRE HUMAN GENETIC THERAPIES, INC., Lexington, MA (US)

(72) Inventors: Gaozhong Zhu, Weston, MA (US); Vinh Nguyen, Chelsea, MA (US); Kris Lowe, Boston, MA (US); Zahra Shahrokh, Weston, MA (US)

(73) Assignee: SHIRE HUMAN GENETIC THERAPIES, INC., Lexington, MA (US)

( * ) Notice: Subject to any disclaimer, the term of this patent is extended or adjusted under 35 U.S.C. 154(b) by 0 days.

(21) Appl. No.: 14/019,850

(22) Filed: Sep. 6, 2013

(65) Prior Publication Data
US 2014/0219987 A1    Aug. 7, 2014

Related U.S. Application Data

(63) Continuation of application No. 12/902,680, filed on Oct. 12, 2010, now Pat. No. 8,673,298, which is a continuation of application No. 11/671,588, filed on Feb. 6, 2007, now Pat. No. 7,833,766.

(60) Provisional application No. 60/771,555, filed on Feb. 7, 2006.

(51) Int. Cl.
*A61K 8/66* (2006.01)
*A61K 38/00* (2006.01)
*A61K 38/17* (2006.01)
*A61K 38/43* (2006.01)
*A61K 38/47* (2006.01)
*A61K 47/26* (2006.01)
*A61K 9/00* (2006.01)
*A61K 9/19* (2006.01)
*A61K 31/7012* (2006.01)
*A61K 38/18* (2006.01)

(52) U.S. Cl.
CPC ............... *A61K 47/26* (2013.01); *A61K 9/0019* (2013.01); *A61K 9/19* (2013.01); *A61K 31/7012* (2013.01); *A61K 38/1825* (2013.01); *A61K 38/47* (2013.01)

(58) Field of Classification Search
None
See application file for complete search history.

(56) References Cited

U.S. PATENT DOCUMENTS

| 5,670,132 | A | 9/1997 | Griffiths et al. |
| 6,074,864 | A | 6/2000 | Ginns et al. |
| 6,340,746 | B1 | 1/2002 | Roberts et al. |
| 6,818,233 | B2 | 11/2004 | Perkes |
| 7,833,766 | B2 * | 11/2010 | Zhu et al. ............... 435/188 |
| 8,673,298 | B2 * | 3/2014 | Zhu et al. ............... 424/130.1 |
| 2004/0063639 | A1 | 4/2004 | Gentz et al. |
| 2004/0202666 | A1 | 10/2004 | Griffiths |
| 2006/0008415 | A1 | 1/2006 | Kaisheva et al. |
| 2006/0194256 | A1 | 8/2006 | Miao et al. |

FOREIGN PATENT DOCUMENTS

| JP | 2003-505430 | 2/2003 |
| WO | WO 92/13067 | 8/1992 |
| WO | WO 94/13311 | 6/1994 |
| WO | WO 97/32591 | 9/1997 |
| WO | WO 98/22136 | 5/1998 |
| WO | WO 00/76480 | 12/2000 |
| WO | WO 01/07078 | 2/2001 |
| WO | WO 2004/069190 | 8/2004 |

OTHER PUBLICATIONS

Andersson et al., "Stabilizing effect of chemical additives against oxidation of lactate dehydrogenase" Biotechno. Appl. Biochem. vol. 32, pp. 145-153 (2000).
Bernier et al., "Stabilization of β-glucosidase by polyhydric alcohols", Journal of Biotechnology, vol. 7(4):293-298 (1988).
Cleland et al., "A Specific Molar Ratio of Stabilizer to Protein is Required for Storage Stability of a Lyophilized Monoclonal Antibody", Journal of Pharmaceutical Sciences, vol. 90(3):310-321, (2001).
Extended European Search Report from European Application Serial No. 10193725.8 dated Jul. 25, 2011.
International Preliminary Report on Patentability mailed Aug. 21, 2008 for PCT Application PCT/US2007/061657.
Lee et al., "The Stabilization of Proteins by Sucrose", The Journal of Biological Chemistry, vol. 256, No. 14, pp. 7193-7201 (1981).
Miroliaei et al., "Sugars protect native and apo yeast alcohol dehydrogenase against irreversible thermoinactivation", Enzyme and Microbial Technology, vol. 29, No. 8-9, pp. 554-559 (2001).
Nguyen et al., "Oxidation Degradation of Protein Pharmaceuticals" ACS Symp. Ser., No. 567, pp. 59-71 (1994).
Passot et al., "Physical characterisation of formulations for the development of two stable freeze-dried proteins during both dried and liquid storage", European Journ. of Pharmaceutics and Biopharmaceutics, vol. 60(3):335-348 (2005).
Tsitsirnpikou et al., "Studies of the effect of organic solvents on the stability of β-glucosidase from *Fusarium oxysporum*", Biotechnology Letters, vol. 16(1):57-62 (1994).
Waldman "Immunotherapy: past, present and future" Nature Medicine 2003 9:269-277.
Wang, "Lyophilization and development of solid protein pharmaceuticals", International Journal of Pharmaceutics, vol. 203(1-2):1-60 (2000).
Written Opinion mailed Aug. 21, 2008 for PCT Application PCT/US2007/061657.

* cited by examiner

*Primary Examiner* — Elizabeth C Kemmerer
(74) *Attorney, Agent, or Firm* — Troutman Sanders LLP

(57) ABSTRACT

Compositions of proteins having free thiols, and methods of making and using such compositions, are described.

31 Claims, No Drawings

STABILIZED COMPOSITIONS OF PROTEINS HAVING A FREE THIOL MOIETY

CROSS-REFERENCE TO RELATED APPLICATIONS

This application is a continuation of U.S. application Ser. No. 12/902,680, filed on Oct. 12, 2010, now U.S. Pat. No. 8,673,298, issued on Mar. 18, 2014, which is a continuation of U.S. application Ser. No. 11/671,588, filed on Feb. 6, 2007, now U.S. Pat. No. 7,833,766, issued on Nov. 16, 2010, which claims priority to U.S. Application Ser. No. 60/771,555, filed on Feb. 7, 2006. The disclosures of the prior applications are considered part of (and are incorporated by reference in) the disclosure of this application.

FIELD OF THE INVENTION

The invention relates to compositions of proteins having free thiols, and to methods of making and methods of using such compositions. The compositions have optimized stability.

BACKGROUND OF THE INVENTION

A drug product (e.g., that contains a protein) can be stored in liquid or lyophilized, i.e., freeze-dried, form. A lyophilized drug product is often reconstituted by adding a suitable administration diluent just prior to patient use.

Active protein may be lost as a result of physical instabilities, including denaturation and aggregation, as well as chemical instabilities, including, for example, hydrolysis, deamidation, and oxidation. The stability of a protein drug in a particular form, e.g., in a liquid or in a lyophilized form, can be an important consideration in selection of a product form.

SUMMARY OF THE INVENTION

In general, the invention features a composition which includes a protein having a free thiol (—S—H) (e.g., on a cysteine residue) and/or other moiety subject to oxidation (e.g., Tyr, Trp, or Met moiety) and a carbohydrate, wherein the carbohydrate is present in an amount sufficient to maintain the stability of the protein, and thereby of the composition. In a particularly preferred embodiment, the moiety to be protected is a free thiol.

Compositions and methods described herein provide for increased stability and storage life by increasing the stability of a protein contained therein.

Compositions described herein, e.g., liquid compositions containing a protein, have prolonged stability. E.g., under pre-selected conditions, e.g., upon storage in a gas tight container, at a temperature of 2-8° C. for a period of up to 3, 6, 9, 12, or 24 months (or in some embodiments longer), a protein in the composition will retain at least 50, 55, 60, 65, 70, 75, 80, 85, 90, 95, 99, or 100% of the stability it had prior to storage. Stability, as used herein, includes parameters such as protein structure (e g, minimizing or preventing changes in protein structure, e.g., protein aggregation or protein degradation (e.g., fragmentation)) and/or a biological activity of the protein, e.g., the ability to convert substrate into product.

Protein stability can be measured, e.g., by measuring protein aggregation, protein degradation, or levels of a biological activity of the protein. Protein aggregation can be determined, e.g., by size exclusion chromatography, non-denaturing PAGE, or other methods for determining size, etc. For example, the composition can have less than a 1, 5, 10, 15, 20, 25, 30, 35, 40, 45, or 50% increase in the amount of protein aggregation (e.g., as measured by size exclusion chromatography) as compared to the amount of protein aggregation that was in the composition prior to storage (e.g., storage at a temperature of 2-8° C. for a period of up to 3, 6, 9, 12, or 24 months (or longer)). Protein degradation can be determined, e.g., by reverse phase HPLC, non-denaturing PAGE, ion-exchange chromatography, peptide mapping, or similar methods. As an example, the composition can have less than a 1, 5, 10, 15, 20, 25, 30, 35, 40, 45, or 50% increase in the amount of protein degradation (e.g., as measured by reverse phase HPLC) as compared to the amount of protein degradation that was in the composition prior to storage (e.g., storage at a temperature of 2-8° C. for a period of up to 3, 6, 9, 12, or 24 months (or longer)). The biological activity of a protein can be measured, e.g., by in vitro or in vivo assays, e.g., ELISA (e.g., to measure binding or enzymatic activity) and other enzymatic assays (e.g., spectrophotometric, fluorimetric, calorimetric, chemiluminescent, radiometric, or chromatographic assays), kinase assays, and so forth. As an example, the composition can have less than a 1, 5, 10, 15, 20, 25, 30, 35, 40, 45, or 50% decrease in a biological activity of the protein (e.g., enzymatic activity, e.g., as measured by an in vitro assay) as compared to the amount of the biological activity that was in the composition prior to storage (e.g., storage at a temperature of 2-8° C. for a period of up to 3, 6, 9, 12, or 24 months (or longer)).

In one aspect, the protein does not modify, e.g., cleave, any other components of the composition. For example, in one preferred embodiment, in a composition containing glucocerebrosidase (GCB), the composition does not contain polysorbate as a surfactant because GCB can recognize polysorbate as a substrate and can cleave polysorbate to release free fatty acids.

Embodiments of the invention have stability comparable to that of a lyophilized composition of the same protein. A liquid composition described herein can have at least 50, 55, 60, 65, 70, 75, 80, 85, 90, 95, 99, or 100% of the level of protein stability (e.g., retained activity) of a lyophilized composition after 3, 6, 12, 18, or 24 months of storage (e.g., if a lyophilized composition has retained 90% of its activity at 18 months, the composition of the invention has retained at least 50, 55, 60, 65, 70, 75, 80, 85, 90, 95, 99, or 100% of that level).

In one aspect, the disclosure features a composition that includes a protein having a free thiol and a carbohydrate, wherein the carbohydrate is present in an amount sufficient to maintain the stability of the protein and wherein the pH of the composition is less than 7.0. In some embodiments, the composition also includes an antioxidant, wherein the antioxidant and carbohydrate are present in amounts sufficient to maintain the stability of the protein, and thereby of the composition, and wherein the pH of the composition is less than 7.0. For example, the antioxidant is cysteine, cysteine hydrochloride (cysteine-HCl), or methionine (e.g., present at between about 0.001 and about 10% (wt/vol)) and the carbohydrate is sucrose or trehalose (e.g., present at between about 1 and about 40% (wt/vol)). In certain embodiments, the pH is in the range of about 4.5 to about 6.5, e.g., preferably between about 5.0 and 6.0, e.g., more preferably between about 5.5 and 5.8 (e.g., about 5.7). In a preferred embodiment, the composition includes a surfactant (e.g., poloxamer 188).

In a preferred embodiment, the pH of the composition is, e.g., between about 4.5 and about 6.5, e.g., between about 5.0 and about 6.0, e.g., between about 5.5 and about 5.8 (e.g., about 5.7).

In certain embodiments, the stability is at least 5-80% greater (e.g., at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80% greater), under pre-selected conditions, than the stability of a composition which differs by lacking the carbohydrate (and the antioxidant, if used).

In certain embodiments, the carbohydrate (and optionally, an antioxidant) is present in an amount sufficient to stabilize the free thiol of the protein (e.g., the protein shows less aggregate formation, e.g., the protein shows about 5%, about 10%, about 15%, about 20%, about 25%, about 30%, about 35%, about 40%, about 45%, about 50%, about 55%, about 60%, about 65%, about 70%, about 75%, about 80%, about 85%, about 90% about 95% or about 99% less aggregate formation under pre-selected conditions than an otherwise identical protein composition that does not contain the carbohydrate (and antioxidant, if used)).

In certain embodiments, the carbohydrate (and optionally, an antioxidant) is present in an amount sufficient to increase the stability of the protein (e.g., the protein shows less aggregate formation, e.g., the protein shows about 5%, about 10%, about 15%, about 20%, about 25%, about 30%, about 35%, about 40%, about 45%, about 50%, about 55%, about 60%, about 65%, about 70%, about 75%, about 80%, about 85%, about 90% about 95% or about 99% less aggregate formation under pre-selected conditions than an otherwise identical protein composition that does not contain the carbohydrate (and antioxidant, if used)).

In certain embodiments, the carbohydrate (and optionally, an antioxidant) is present in an amount sufficient to inhibit the reaction of a free thiol on a first molecule of the protein with a free thiol on a second molecule of the protein to form an aggregate.

In certain embodiments, the carbohydrate (and optionally, an antioxidant) is present in an amount sufficient to inhibit the formation of an aggregate formed by the reaction of a free thiol on a first molecule of the protein with a free thiol on a second molecule of the protein by at least 5-80% (e.g., at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80% greater), under pre-selected conditions, as compared to the same composition lacking the carbohydrate (and the antioxidant, if present).

In certain embodiments, the carbohydrate (and optionally, an antioxidant) is present in an amount sufficient that upon storage, in a gas tight container, at a temperature of 2-8° C., for a period of 6 months, the composition will retain at least 50, 55, 60, 65, 70, 75, 80, 85, 90, 95, 99, or 100% of the stability the composition had prior to storage. In a preferred embodiment, the storage occurs in darkness.

In certain embodiments, the carbohydrate (and optionally, an antioxidant) is present in an amount sufficient to have stability comparable to that of a lyophilized composition comprising about 0.01% polysorbate-20, pH 6.0, 50 mM Citrate. In certain embodiments, the composition further includes about 1-40% (e.g., about 5 to about 30%, e.g., about 8 to about 24%, e.g., about 16%, e.g., about 3-5% weight per volume (w/v)) of a carbohydrate, e.g., sucrose or trehalose. In some embodiments, the carbohydrate is preferably sucrose.

In a preferred embodiment, the composition is a liquid.

In certain embodiments, the composition contains less than about 10% $O_2$ (e.g., less than about 5% $O_2$, e.g., less than about 2% $O_2$). In a preferred embodiment, the amount of dissolved $O_2$ is less than the amount of dissolved inert gases in the composition.

In certain embodiments, the composition is made by a method comprising physical removal of $O_2$ from the composition (e.g., degassing the composition, purging a solution with a gas other than $O_2$, e.g., with an inert gas (e.g., with $N_2$ or Ar), e.g., bubbling the gas other than $O_2$ (e.g., $N_2$ or Ar) through the composition).

In certain embodiments, the protein in the composition that contains a free thiol has zero, two, four, six, or more thiol groups which form sulfhydryl bridges. In certain embodiments, the protein containing a free thiol has two, three, or more free thiol groups and has zero, two, four, or more thiol groups which form sulfhydryl bridges, per active unit of protein.

In certain embodiments, the protein containing a free thiol is selected from the group consisting of glucocerebrosidase (GCB), basic fibroblast growth factor (bFGF), acidic fibroblast growth factor (aFGF), hemoglobin, thioredoxin, calcium- and integrin-binding protein 1 (CIB1), beta-lactoglobulin B, beta-lactoglobulin AB, serum albumin, antibodies (e.g., human antibodies, e.g., IgA (e.g., dimeric IgA), IgG (e.g., IgG2), and IgM; recombinant human antibodies), antibody fragments (e.g., Fab' fragments, F(ab')$_2$ fragments, single-chain Fv fragments (scFv)), antibodies and antibody fragments (e.g., Fab', e.g., monoclonal antibody fragment C46.3; and scFv) engineered (e.g., so that the antibody or antibody fragment can be labeled, e.g., with 99mTc, to clinical imaging) to introduce cysteine residues (e.g., in the third heavy chain constant domain, e.g., at position 442 in EU/OU numbering; monoclonal antibody MN-14 (a high-affinity anti-carcinoembryonic antigen (CEA)mab)), core 2 beta 1,6-N-acetylglucosaminyltransferase-M (C2GnT-M), core 2 beta 1,6-N-acetylglucosaminyltransferase-I (C2GnT-I), platelet-derived growth factor receptor-beta (PDGF-beta), adenine nucleotide translocase (ANT), p53 tumor suppressor protein, gluten proteins, acid sphingomyelinase (recombinant acid sphyngomyelinase), desfuroylceftiofur (DFC), apolipoprotein B100 (apoB) and other low density lipoprotein domains, apolipoprotein A-I variants (e.g., apolipoprotein A-I (Milano) and apolipoprotein A-I (Paris)), hypoxia-inducible factor-1 alpha (HIF-1 alpha), von Willebrand factor (VWF), proteins and peptide mimetics that contain the CAAX motif (e.g., Ras), mucolytics, carboxypeptidase Y, cathepsin B, cathepsin C, skeletal muscle $Ca^{2+}$ release channel/ryanodine receptor (RyR1), nuclear factor kappa B (NF-KB), AP-1, protein-disulfide isomerase (PDI), glycoprotein 1b alpha (GP1b alpha), calcineurin (CaN), fibrillin-1, CD4, S100A3 (also known as S100E), ionotropic glutamate receptors, human inter-alpha-inhibitor heavy chain 1, alpha2-antiplasmin (alpha2AP), thrombospondin (also known as glycoprotein G), gelsolin, mucins, creatine kinase (e.g., S-thiomethyl-modified creatine kinase), Factor VIII, phospholipase D (PLD), insulin receptor beta subunit, acetylcholinesterase, prochymosin, modified alpha 2-macroglobulin (alpha 2M) (e.g., proteinase- or methylamine-reacted alpha 2M), glutathione reductase (GR), complement component C2 (e.g., 2a), complement component C3 (e.g., C3b), complement component 4 (e.g., 4d), complement Factor B (e.g., Bb), alpha-lactalbumin, beta-D-galactosidase, endoplasmic reticulum $Ca^{2+}$-ATPase, RNase inhibitor, lipocortin 1 (also known as annexin 1), proliferating cell nuclear antigen (PCNA), actin (e.g., globular actin), coenzyme A (CoA), acyl-CoA synthetase (e.g., butyryl-coenzyme A synthetase), 3-2trans-enoyl-CoA-isomerase precursor, atrial natriuretic factor (ANF)-sensitive guanylate cyclase, Pz-peptidase, aldehyde dehydrogenase (e.g., acylated aldehyde dehydrogenase), P-450 and NADPH-P-450 reductase, glyceraldehydes-3-phosphate dehydrogenase (GAPDH), 6-pyruvoyl tetrahydropterin synthetase, lutropin receptor, low moleculat weight acid phosphatase, serum cholinesterase (BChE), adrenodoxin, hyaluronidase, carnitine acyltransferases, interleukin-2 (IL-2), phosphoglycerate kinase, insulin-degrading enzyme (IDE), cytochrome c1 heme subunit, S-protein, valyl-tRNA synthetase (VRS), alpha-amylase I, muscle AMP deaminase, lactate dehydrogenase, and somatostatin-binding protein.

In a preferred embodiment, the protein containing a free thiol is GCB.

In another preferred embodiment, the protein containing a free thiol is bFGF.

In one aspect, the disclosure features a liquid composition of GCB that includes GCB, and a carbohydrate at a pH less than 7.0, was produced by exposing the composition to an inert gas (e.g., $N_2$), and the inert gas is present in a concentration higher than in the ambient atmosphere, e.g., the composition contains at least about 85%, 90%, 95%, or 99%, or preferably 100% inert gas. In certain embodiments, the composition also includes an antioxidant. For example, the antioxidant is cysteine, cysteine-HCl, or methionine (e.g., present at between about 0.001 and about 10% (wt/vol)) and the carbohydrate is sucrose or trehalose (e.g., present at between about 1 and about 40% (wt/vol)). In certain embodiments, the pH is in the range of about 4.5 to about 6.5, e.g., preferably between about 5.0 and about 6.0, e.g., more preferably between about 5.5 and about 5.8 (e.g., about 5.7). In certain embodiments, the composition also contains a surfactant (e.g., poloxymer 188).

In one aspect, the disclosure features a composition that includes a protein having a free thiol and a carbohydrate, and is at a pH below the pKa of a free thiol on the protein, wherein the carbohydrate is present in an amount sufficient to increase the stability of the protein at the pH.

In certain embodiments, the stability is at least 5-80% greater (e.g., at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80% greater), under pre-selected conditions, than the stability of a composition which lacks the carbohydrate and which has a pH above the pKa of a free thiol on the protein.

In certain embodiments, the carbohydrate is present in an amount sufficient to stabilize the free thiol of the protein.

In certain embodiments, the carbohydrate is present in an amount sufficient to inhibit the reaction of a free thiol on a first molecule of the protein with a free thiol on a second molecule of the protein to form an aggregate.

In certain embodiments, the carbohydrate is present in an amount sufficient to inhibit the formation of an aggregate formed by the reaction of a free thiol on a first molecule of the protein with a free thiol on a second molecule of the protein by at least 50, 55, 60, 65, 70, 75, 80, 85, 90, 95, 99, or 100%, under pre-selected conditions, as compared to the same composition lacking the carbohydrate.

In a preferred embodiment, the carbohydrate is present in an amount sufficient that upon storage in darkness, in a gas tight container, at a temperature of 2-8° C. for a period of up to 3, 6, 9, 12, or 24 months (or longer), the composition will retain at least 50, 55, 60, 65, 70, 75, 80, 85, 90, 95, 99, or 100% of the stability it had prior to storage.

In certain embodiments, the carbohydrate is present in an amount sufficient for the composition to have stability comparable to that of a lyophilized composition.

In a preferred embodiment, the composition is a liquid.

In certain embodiments, the composition contains less than 10% $O_2$ (e.g., less than 5% $O_2$, e.g., less than 2% $O_2$). In certain embodiments, the amount of dissolved $O_2$ is less than the amount of dissolved inert gases in the composition.

In certain embodiments, the composition is made by a method comprising physical removal of $O_2$ from the composition (e.g., degassing the composition, purging a solution with a gas other than $O_2$, e.g., with an inert gas (e.g., with $N_2$ or Ar), e.g., bubbling the gas other than $O_2$ (e.g., $N_2$ or Ar) through the composition).

In certain embodiments, the protein in the composition that contains a free thiol has two, three, four, five, or more free thiol groups per active unit of protein.

In certain embodiments, the protein in the composition that contains a free thiol has two, four, six, or more thiol groups which form sulfhydryl bridges per active unit (e.g., dimer) of protein. In certain embodiments, the protein that contains a free thiol has two, three, or more free thiol groups and has two, four, or more thiol groups which form sulfhydryl bridges, per active unit of protein.

In certain embodiments, the protein containing a free thiol is selected from the group consisting of glucocerebrosidase (GCB), basic fibroblast growth factor (bFGF), acidic fibroblast growth factor (aFGF), hemoglobin, thioredoxin, calcium- and integrin-binding protein 1 (CIB1), beta-lactoglobulin B, beta-lactoglobulin AB, serum albumin, antibodies (e.g., human antibodies, e.g., IgA (e.g., dimeric IgA), IgG (e.g., IgG2), and IgM; recombinant human antibodies), antibody fragments (e.g., Fab' fragments, F(ab')$_2$ fragments, single-chain Fv fragments (scFv)), antibodies and antibody fragments (e.g., Fab', e.g., monoclonal antibody fragment C46.3; and scFv) engineered (e.g., so that the antibody or antibody fragment can be labeled, e.g., with 99mTc, to clinical imaging) to introduce cysteine residues (e.g., in the third heavy chain constant domain, e.g., at position 442 in EU/OU numbering; monoclonal antibody MN-14 (a high-affinity anti-carcinoembryonic antigen (CEA)mab)), core 2 beta 1,6-N-acetylglucosaminyltransferase-M (C2GnT-M), core 2 beta 1,6-N-acetylglucosaminyltransferase-I (C2GnT-I), platelet-derived growth factor receptor-beta (PDGF-beta), adenine nucleotide translocase (ANT), p53 tumor suppressor protein, gluten proteins, acid sphingomyelinase (recombinant acid sphyngomyelinase), desfuroylceftiofur (DFC), apolipoprotein B100 (apoB) and other low density lipoprotein domains, apolipoprotein A-I variants (e.g., apolipoprotein A-I (Milano) and apolipoprotein A-I (Paris)), hypoxia-inducible factor-1 alpha (HIF-1 alpha), von Willebrand factor (VWF), proteins and peptide mimetics that contain the CAAX motif (e.g., Ras), mucolytics, carboxypeptidase Y, cathepsin B, cathepsin C, skeletal muscle $Ca^{2+}$ release channel/ryanodine receptor (RyR1), nuclear factor kappa B (NF-KB), AP-1, protein-disulfide isomerase (PDI), glycoprotein 1b alpha (GP1b alpha), calcineurin (CaN), fibrillin-1, CD4, S100A3 (also known as S100E), ionotropic glutamate receptors, human inter-alpha-inhibitor heavy chain 1, alpha2-antiplasmin (alpha2AP), thrombospondin (also known as glycoprotein G), gelsolin, mucins, creatine kinase (e.g., S-thiomethyl-modified creatine kinase), Factor VIII, phospholipase D (PLD), insulin receptor beta subunit, acetylcholinesterase, prochymosin, modified alpha 2-macroglobulin (alpha 2M) (e.g., proteinase- or methylamine-reacted alpha 2M), glutathione reductase (GR), complement component C2 (e.g., 2a), complement component C3 (e.g., C3b), complement component 4 (e.g., 4d), complement Factor B (e.g., Bb), alpha-lactalbumin, beta-D-galactosidase, endoplasmic reticulum $Ca^{2+}$-ATPase, RNase inhibitor, lipocortin 1 (also known as annexin 1), proliferating cell nuclear antigen (PCNA), actin (e.g., globular actin), coenzyme A (CoA), acyl-CoA synthetase (e.g., butyryl-coenzyme A synthetase), 3-2trans-enoyl-CoA-isomerase precursor, atrial natriuretic factor (ANF)-sensitive guanylate cyclase, Pz-peptidase, aldehyde dehydrogenase (e.g., acylated aldehyde dehydrogenase), P-450 and NADPH-P-450 reductase, glyceraldehydes-3-phosphate dehydrogenase (GAPDH), 6-pyruvoyl tetrahydropterin synthetase, lutropin receptor, low moleculat weight acid phosphatase, serum cholinesterase (BChE), adrenodoxin, hyaluronidase, carnitine acyltransferases, interleukin-2 (IL-2), phosphoglycerate kinase, insulin-degrading enzyme (IDE), cytochrome c1 heme subunit, S-protein, valyl-tRNA synthetase (VRS), alpha-amylase I, muscle AMP deaminase, lactate dehydrogenase, and somatostatin-binding protein.

In a preferred embodiment, the protein containing a free thiol is GCB.

In another preferred embodiment, the protein containing a free thiol is bFGF.

In one aspect, the disclosure features a liquid composition of GCB that includes GCB and a carbohydrate and is at a pH between about 0 and about 7, and the carbohydrate is present in an amount sufficient to maintain the biophysical/biochemical integrity (e.g., molecular weight, charge distribution) and bioactivity characteristics/properties of the GCB at the pH. For example, the composition retains at least 50, 55, 60, 65, 70, 75, 80, 85, 90, 95, 99, or 100% of the biological activity it had prior to storage (e.g., storage at a temperature of 2-8° C. for a period of up to 3, 6, 9, 12, or 24 months (or longer)). As another example, at least 50, 55, 60, 65, 70, 75, 80, 85, 90, 95, 99, or 100% of the proteins in the composition retain the average molecular weight or average charge distribution that the proteins had prior to storage (e.g., storage at a temperature of 2-8° C. for a period of up to 3, 6, 9, 12, or 24 months (or longer)).

In certain embodiments, the pH is in the range of about 4.5 to about 6.5, e.g., about 5.0 to about 6.0 (e.g., the pH is about 5.5 to about 5.8, e.g., about 5.7).

In a preferred embodiment, the carbohydrate is sucrose or trehalose (e.g., present in an amount between about 1 and about 40%, e.g., between about 3% and about 5% (wt/vol)).

In one aspect, the disclosure features a liquid composition of GCB that includes GCB, an antioxidant, a carbohydrate, at a pH between 4.5-6.5, and the composition was produced by exposing the composition to an inert gas (e.g., $N_2$ or Ar). In certain embodiments, the pH is in the range of about 4.5 to about 6.5, e.g., about 5.0 to about 6.0 (e.g., the pH is about 5.5 to about 5.8, e.g., about 5.7).

In certain embodiments, the liquid composition includes about 0.1-40 mg/ml GCB (e.g., more preferably about 0.5 to about 10 mg/ml, e.g., about 2 to about 8 mg/ml or about 5 mg/ml) (e.g., about 2 mg/ml), about 0.001-10% cysteine (e.g., about 0.075%), about 1-40% sucrose (e.g., about 16%), at a pH of about 5.5-6.0 (e.g., about 5.7), and the level of dissolved $O_2$ is less than about 10% (e.g., less than about 5%, e.g., less than about 2%).

In a preferred embodiment, the composition also includes a surfactant (e.g., poloxamer 188).

In one aspect, the disclosure features a gas tight container that contains a protein component and a headspace wherein the protein component is a protein having a free thiol and the headspace is at least 90%, 95% or 99% (vol/vol) an inert gas.

In certain embodiments, the gas tight container is a prefilled syringe, a vial, or an ampoule. In a more preferred embodiment, the prefilled syringe is a needleless syringe.

In certain embodiments, the protein containing a free thiol is selected from the group consisting of glucocerebrosidase (GCB), basic fibroblast growth factor (bFGF), acidic fibroblast growth factor (aFGF), hemoglobin, thioredoxin, calcium- and integrin-binding protein 1 (CIB1), beta-lactoglobulin B, beta-lactoglobulin AB, serum albumin, antibodies (e.g., human antibodies, e.g., IgA (e.g., dimeric IgA), IgG (e.g., IgG2), and IgM; recombinant human antibodies), antibody fragments (e.g., Fab' fragments, $F(ab')_2$ fragments, single-chain Fv fragments (scFv)), antibodies and antibody fragments (e.g., Fab', e.g., monoclonal antibody fragment C46.3; and scFv) engineered (e.g., so that the antibody or antibody fragment can be labeled, e.g., with 99mTc, to clinical imaging) to introduce cysteine residues (e.g., in the third heavy chain constant domain, e.g., at position 442 in EU/OU numbering; monoclonal antibody MN-14 (a high-affinity anti-carcinoembryonic antigen (CEA)mab)), core 2 beta 1,6-N-acetylglucosaminyltransferase-M (C2GnT-M), core 2 beta 1,6-N-acetylglucosaminyltransferase-I (C2GnT-I), platelet-derived growth factor receptor-beta (PDGF-beta), adenine nucleotide translocase (ANT), p53 tumor suppressor protein, gluten proteins, acid sphingomyelinase (recombinant acid sphyngomyelinase), desfuroylceftiofur (DFC), apolipoprotein B100 (apoB) and other low density lipoprotein domains, apolipoprotein A-I variants (e.g., apolipoprotein A-I (Milano) and apolipoprotein A-I (Paris)), hypoxia-inducible factor-1 alpha (HIF-1 alpha), von Willebrand factor (VWF), proteins and peptide mimetics that contain the CAAX motif (e.g., Ras), mucolytics, carboxypeptidase Y, cathepsin B, cathepsin C, skeletal muscle $Ca^{2+}$ release channel/ryanodine receptor (RyR1), nuclear factor kappa B (NF-KB), AP-1, protein-disulfide isomerase (PDI), glycoprotein 1b alpha (GP1b alpha), calcineurin (CaN), fibrillin-1, CD4, S100A3 (also known as S100E), ionotropic glutamate receptors, human inter-alpha-inhibitor heavy chain 1, alpha2-antiplasmin (alpha2AP), thrombospondin (also known as glycoprotein G), gelsolin, mucins, creatine kinase (e.g., S-thiomethyl-modified creatine kinase), Factor VIII, phospholipase D (PLD), insulin receptor beta subunit, acetylcholinesterase, prochymosin, modified alpha 2-macroglobulin (alpha 2M) (e.g., proteinase- or methylamine-reacted alpha 2M), glutathione reductase (GR), complement component C2 (e.g., 2a), complement component C3 (e.g., C3b), complement component 4 (e.g., 4d), complement Factor B (e.g., Bb), alpha-lactalbumin, beta-D-galactosidase, endoplasmic reticulum $Ca^{2+}$-ATPase, RNase inhibitor, lipocortin 1 (also known as annexin 1), proliferating cell nuclear antigen (PCNA), actin (e.g., globular actin), coenzyme A (CoA), acyl-CoA synthetase (e.g., butyryl-coenzyme A synthetase), 3-2trans-enoyl-CoA-isomerase precursor, atrial natriuretic factor (ANF)-sensitive guanylate cyclase, Pz-peptidase, aldehyde dehydrogenase (e.g., acylated aldehyde dehydrogenase), P-450 and NADPH-P-450 reductase, glyceraldehydes-3-phosphate dehydrogenase (GAPDH), 6-pyruvoyl tetrahydropterin synthetase, lutropin receptor, low moleculat weight acid phosphatase, serum cholinesterase (BChE), adrenodoxin, hyaluronidase, carnitine acyltransferases, interleukin-2 (IL-2), phosphoglycerate kinase, insulin-degrading enzyme (IDE), cytochrome c1 heme subunit, S-protein, valyl-tRNA synthetase (VRS), alpha-amylase I, muscle AMP deaminase, lactate dehydrogenase, and somatostatin-binding protein.

In a preferred embodiment, the protein containing a free thiol is GCB.

In another preferred embodiment, the protein containing a free thiol is bFGF.

In one aspect, the disclosure features a method of packaging a composition that includes contacting a free thiol containing protein with an inert gas (e.g., $N_2$ or Ar) to reduce the amount of a reactive species (e.g., $O_2$), and introducing the protein and the inert gas into a gas tight container. The term "reactive species" includes molecules or ions formed by the incomplete one-electron reduction of oxygen. These reactive species include $O_2$; superoxides; peroxides; hydroxyl radical; and hypochlorous acid.

In a preferred embodiment, the inert gas is $N_2$ or Ar and the reactive species is $O_2$.

In certain embodiments, the free thiol containing protein is selected from the group consisting of glucocerebrosidase (GCB), basic fibroblast growth factor (bFGF), acidic fibroblast growth factor (aFGF), hemoglobin, thioredoxin, calcium- and integrin-binding protein 1 (CIB1), beta-lactoglobulin B, beta-lactoglobulin AB, serum albumin, antibodies (e.g., human antibodies, e.g., IgA (e.g., dimeric IgA), IgG (e.g., IgG2), and IgM; recombinant human antibodies), antibody fragments (e.g., Fab' fragments, F(ab')$_2$ fragments, single-chain Fv fragments (scFv)), antibodies and antibody fragments (e.g., Fab', e.g., monoclonal antibody fragment C46.3; and scFv) engineered (e.g., so that the antibody or antibody fragment can be labeled, e.g., with 99mTc, to clinical imaging) to introduce cysteine residues (e.g., in the third heavy chain constant domain, e.g., at position 442 in EU/OU numbering; monoclonal antibody MN-14 (a high-affinity anti-carcinoembryonic antigen (CEA)mab)), core 2 beta 1,6-N-acetylglucosaminyltransferase-M (C2GnT-M), core 2 beta 1,6-N-acetylglucosaminyltransferase-I (C2GnT-I), platelet-derived growth factor receptor-beta (PDGF-beta), adenine nucleotide translocase (ANT), p53 tumor suppressor protein, gluten proteins, acid sphingomyelinase (recombinant acid sphyngomyelinase), desfuroylceftiofur (DFC), apolipoprotein B100 (apoB) and other low density lipoprotein domains, apolipoprotein A-I variants (e.g., apolipoprotein A-I (Milano) and apolipoprotein A-I (Paris)), hypoxia-inducible factor-1 alpha (HIF-1 alpha), von Willebrand factor (VWF), proteins and peptide mimetics that contain the CAAX motif (e.g., Ras), mucolytics, carboxypeptidase Y, cathepsin B, cathepsin C, skeletal muscle $Ca^{2+}$ release channel/ryanodine receptor (RyR1), nuclear factor kappa B (NF-KB), AP-1, protein-disulfide isomerase (PDI), glycoprotein 1b alpha (GP1b alpha), calcineurin (CaN), fibrillin-1, CD4, S100A3 (also known as S100E), ionotropic glutamate receptors, human inter-alpha-inhibitor heavy chain 1, alpha2-antiplasmin (alpha2AP), thrombospondin (also known as glycoprotein G), gelsolin, mucins, creatine kinase (e.g., S-thiomethyl-modified creatine kinase), Factor VIII, phospholipase D (PLD), insulin receptor beta subunit, acetylcholinesterase, prochymosin, modified alpha 2-macroglobulin (alpha 2M) (e.g., proteinase- or methylamine-reacted alpha 2M), glutathione reductase (GR), complement component C2 (e.g., 2a), complement component C3 (e.g., C3b), complement component 4 (e.g., 4d), complement Factor B (e.g., Bb), alpha-lactalbumin, beta-D-galactosidase, endoplasmic reticulum $Ca^{2+}$-ATPase, RNase inhibitor, lipocortin 1 (also known as annexin 1), proliferating cell nuclear antigen (PCNA), actin (e.g., globular actin), coenzyme A (CoA), acyl-CoA synthetase (e.g., butyryl-coenzyme A synthetase), 3-2trans-enoyl-CoA-isomerase precursor, atrial natriuretic factor (ANF)-sensitive guanylate cyclase, Pz-peptidase, aldehyde dehydrogenase (e.g., acylated aldehyde dehydrogenase), P-450 and NADPH-P-450 reductase, glyceraldehydes-3-phosphate dehydrogenase (GAPDH), 6-pyruvoyl tetrahydropterin synthetase, lutropin receptor, low moleculat weight acid phosphatase, serum cholinesterase (BChE), adrenodoxin, hyaluronidase, carnitine acyltransferases, interleukin-2 (IL-2), phosphoglycerate kinase, insulin-degrading enzyme (IDE), cytochrome c1 heme subunit, S-protein, valyl-tRNA synthetase (VRS), alpha-amylase I, muscle AMP deaminase, lactate dehydrogenase, and somatostatin-binding protein.

In a preferred embodiment, the protein containing a free thiol is GCB.

In another preferred embodiment, the protein containing a free thiol is bFGF.

In one aspect, the disclosure features a method of treating a patient (e.g., a patient in need of treatment with a free-thiol containing protein, e.g., a patient with a deficiency of the free-thiol protein) that includes administering a composition described herein, e.g., a composition containing a free-thiol protein (e.g., GCB), to a patient. For example, a pharmaceutical composition that is administered to a patient can include a composition described herein, e.g., in a therapeutically-effective amount.

In a preferred embodiment, the administration is by IV infusion or subcutaneous.

In one embodiment, a composition described herein that contains a free-thiol protein (e.g., GCB) is used in therapy.

In one embodiment, a composition described herein that contains a free-thiol protein (e.g., GCB) is used for the manufacture of a medicament for the treatment of a condition in which there is a need for the free-thiol containing protein (e.g., the use of a GCB composition described herein for the treatment of a glucocerebrosidase deficiency, e.g., Gaucher disease). For example, a medicament for administration to a patient can include a composition described herein, e.g., in a therapeutically-effective amount.

In one aspect, the disclosure features a method of treating a patient having a glucocerebrosidase deficiency that includes administering a GCB composition described herein.

In certain embodiments, the glucocerebrosidase deficiency is Gaucher disease.

Unless otherwise defined, all technical and scientific terms used herein have the same meaning as commonly understood by one of ordinary skill in the art to which this invention belongs. Although methods and materials similar or equivalent to those described herein can be used in the practicing or testing of the present invention, suitable materials and methods are described below. All cited publications, patent applications, patents, and other references mentioned herein are incorporated by reference in their entirety. In case of conflict, the present specification, including definitions, will control. In addition, the materials, methods, and examples are illustrative only and not intended to be limiting.

Other features, objects, and advantages of the invention will be apparent from the description and from the claims.

DETAILED DESCRIPTION

Overview

Compositions of free thiol-containing proteins (e.g., GCB) are relatively unstable as liquid compositions. The three exposed free thiol groups in GCB can undergo reactions which lead to reduction in stability, e.g., by aggregation of GCB molecules. For example, in buffer at a pH of 6, typically 1-2% of the protein has aggregated upon one month of storage and about 15% has aggregated after 6 months of storage. While not wishing to be bound strictly by theory or mechanism, it is believed that a number of factors contribute to protein instability, e.g., the aggregation reaction: For example, free $O_2$ in solution can accelerate cross-linking of the free thiol groups, leading to aggregation. If the reaction of the free thiol groups is reduced and/or if the protein can be made more compact, for example, by burying cysteine residues in hydrophobic domains, protein aggregation can be reduced. In addition, protein degradation (e.g., fragmentation) can be reduced.

Embodiments described herein include one or more measures to address one or more of these issues. As examples, various factors have been addressed to increase the stability of compositions (e.g., liquid compositions) of free thiol-containing proteins, for example: the presence of reactive species (e.g., free $O_2$) in solution, the availability of free sulfhydryl groups (e.g., free thiols) on the protein, the protein conformation, and pH. One, two, three, four, or all of these factors can be altered or controlled to increase the stability of a protein of interest.

Free Thiol-Containing Proteins

Free thiol-bearing proteins are proteins which in active form have one or more —S—H moieties. In preferred embodiments, the —S—H moiety is accessible to a reactant and can react with that reactant, e.g., a reducing agent such as cysteine, under conditions which are optimal for stability. Alternatively, the —S—H moiety can react with a reactant under physiological conditions with one or more biological fluids that it comes into contact with when administered to a patient, e.g., the moiety is accessible for reaction in blood.

A particularly preferred free thiol-containing protein is glucocerebrosidase (GCB). The structure of GCB in solution provides relatively accessible (as opposed to buried or hindered) free —S—H moieties, which promotes reactions with the —S—H moiety.

Another particularly preferred free thiol-containing protein is basic fibroblast growth factor (bFGF).

Other examples of free thiol-containing proteins include: acidic fibroblast growth factor (aFGF), hemoglobin, thioredoxin, calcium- and integrin-binding protein 1 (CIB1), beta-lactoglobulin B, beta-lactoglobulin AB, serum albumin, antibodies (e.g., human antibodies, e.g., IgA (e.g., dimeric IgA), IgG (e.g., IgG2), and IgM; recombinant human antibodies), antibody fragments (e.g., Fab' fragments, F(ab')$_2$ fragments, single-chain Fv fragments (scFv)), antibodies and antibody fragments (e.g., Fab', e.g., monoclonal antibody fragment C46.3; and scFv) that have been engineered (e.g., so that the antibody or antibody fragment can be labeled, e.g., with 99mTc, for clinical imaging) to introduce cysteine residues (e.g., in the third heavy chain constant domain, e.g., at position 442 in EU/OU numbering; monoclonal antibody MN-14 (a high-affinity anti-carcinoembryonic antigen (CEA)mab)), core 2 beta 1,6-N-acetylglucosaminyltransferase-M (C2GnT-M), core 2 beta 1,6-N-acetylglucosaminyltransferase-I (C2GnT-I), platelet-derived growth factor receptor-beta (PDGF-beta), adenine nucleotide translocase (ANT), p53 tumor suppressor protein, gluten proteins, acid sphingomyelinase (recombinant acid sphyngomyelinase), desfuroyl-ceftiofur (DFC), apolipoprotein B100 (apoB) and other low density lipoprotein domains, apolipoprotein A-I variants (e.g., apolipoprotein A-I (Milano) and apolipoprotein A-I (Paris)), hypoxia-inducible factor-1 alpha (HIF-1 alpha), von Willebrand factor (VWF), proteins and peptide mimetics that contain the CAAX motif (e.g., Ras), mucolytics, carboxypeptidase Y, cathepsin B, cathepsin C, skeletal muscle $Ca^{2+}$ release channel/ryanodine receptor (RyR1), nuclear factor kappa B (NF-KB), AP-1, protein-disulfide isomerase (PDI), glycoprotein 1b alpha (GP1b alpha), calcineurin (CaN), fibrillin-1, CD4, S100A3 (also known as S100E), ionotropic glutamate receptors, human inter-alpha-inhibitor heavy chain 1, alpha2-antiplasmin (alpha2AP), thrombospondin (also known as glycoprotein G), gelsolin, mucins, creatine kinase (e.g., S-thiomethyl-modified creatine kinase), Factor VIII, phospholipase D (PLD), insulin receptor beta subunit, acetylcholinesterase, prochymosin, modified alpha 2-macroglobulin (alpha 2M) (e.g., proteinase- or methylamine-reacted alpha 2M), glutathione reductase (GR), complement component C2 (e.g., 2a), complement component C3 (e.g., C3b), complement component 4 (e.g., 4d), complement Factor B (e.g., Bb), alpha-lactalbumin, beta-D-galactosidase, endoplasmic reticulum $Ca^{2+}$-ATPase, RNase inhibitor, lipocortin 1 (also known as annexin 1), proliferating cell nuclear antigen (PCNA), actin (e.g., globular actin), coenzyme A (CoA), acyl-CoA synthetase (e.g., butyryl-coenzyme A synthetase), 3-2trans-enoyl-CoA-isomerase precursor, atrial natriuretic factor (ANF)-sensitive guanylate cyclase, Pz-peptidase, aldehyde dehydrogenase (e.g., acylated aldehyde dehydrogenase), P-450 and NADPH-P-450 reductase, glyceraldehydes-3-phosphate dehydrogenase (GAPDH), 6-pyruvoyl tetrahydropterin synthetase, lutropin receptor, low moleculat weight acid phosphatase, serum cholinesterase (BChE), adrenodoxin, hyaluronidase, carnitine acyltransferases, interleukin-2 (IL-2), phosphoglycerate kinase, insulin-degrading enzyme (IDE), cytochrome c1 heme subunit, S-protein, valyl-tRNA synthetase (VRS), alpha-amylase I, muscle AMP deaminase, lactate dehydrogenase, and somatostatin-binding protein. Also included are fragments of such proteins (e.g., active domains, structural domains, dominant negative fragments, and so forth). The proteins containing a free thiol group can be naturally occurring proteins, recombinant proteins, proteins modified (e.g., by recombinant DNA technology) to contain a cysteine residue, or proteins chemically or enzymatically treated so that a sulfhydryl moiety on a cysteine residue is in a reduced state, i.e., to have a free —S—H moiety.

In some embodiments, a composition described herein includes a protein having a naturally occurring sequence. In other embodiments, the sequence of the protein will differ at 1, 2, 3, 4, 5, or up to 10 amino acid residues from a naturally occurring sequence. In other embodiments, the amino acid sequence of the protein will differ by 1, 2, 3, 4, 5, or up to 10% from a naturally occurring sequence.

Reactive Species Removal

Reactive species, e.g., $O_2$ or peroxides, dissolved in solution can decrease the stability of a protein in the composition, e.g., by promoting protein aggregation. However, even in the absence of $O_2$, free —S—H moieties can cross-link.

To increase protein stability, reactive species, e.g., $O_2$, in a solution can be removed, e.g., chemically, by the use of $O_2$ scavengers, e.g., sulfites. Chemical scavengers are often less desirable as they can cause protein degradation. $O_2$ can also be removed physically from a solution, e.g., by degassing the solution, e.g., by applying a vacuum to the solution to remove the $O_2$ from solution and replacing it with an inert gas, e.g., nitrogen or argon. Reduction of $O_2$ levels can also be accomplished physically by purging a solution with a gas other than $O_2$, e.g., an inert gas, e.g., nitrogen or argon. Purging can be accomplished by bubbling the gas through the solution to be purged of $O_2$.

With protein (e.g., GCB) compositions, bubbling or other manipulations which result in interfaces between a gas and a protein-containing solution are often avoided in the treatment of proteins because they can denature proteins, however, these manipulations have been discovered to be well-tolerated in the GCB methods disclosed herein.

$O_2$ removal can be combined with minimization of contact of a solution with $O_2$, e.g., by manipulation and storage under conditions which minimize the presence of $O_2$, e.g., filling of containers under a gas other than $O_2$, e.g., an inert gas, e.g., nitrogen or argon, or the sealing of containers with such a gas. In general, it is desirable to minimize the contact of the solution with $O_2$ prior to administration to the patient. $O_2$ levels in head space should be reduced to less than about 10%, preferably less than about 5%, and more preferably less than about 2%.

Removal of reactive species may also result in increased protein stability, e.g., by minimizing oxidation of other moieties as well, e.g., Tyr, Trp, and/or Met residues. In particular, it is desirable to minimize oxidation of these moieties in GCB.

One can test a candidate method for removal of $O_2$ by providing a composition containing 2 mg/ml GCB, 0.075% cysteine (as an antioxidant), 16% sucrose (to decrease —S—H availability), adjusting the pH to 5.7, and applying the candidate method. The stability of the GCB composition produced by the candidate method, measured, e.g., as a percent aggregation or degradation, at a predetermined time is compared with one or more standards. For example, a suitable standard would be a composition similar to the test conditions except that an $O_2$ removal method is not applied. The stabilities of the treated (wherein the candidate $O_2$ removal method is applied) and untreated (wherein an $O_2$ removal method is not applied) compositions are compared. Suitability can be shown by the test treatment increasing stability as compared with this standard. Another standard can be a composition similar to the test composition except that in place of the candidate method of removal, $O_2$ is removed by a method described herein, for example, by purging or degassing with an inert gas. Suitability can be shown by the candidate method having comparable or better effects on stability than the method described herein.

Protein stability can be measured, e.g., by measuring protein aggregation or protein degradation. Protein aggregation can be determined, e.g., by size exclusion chromatography, non-denaturing PAGE, or other methods for determining size, etc. Protein degradation can be determined, e.g., by reverse phase HPLC, non-denaturing PAGE, ion-exchange chromatography, peptide mapping, or similar methods.

Antioxidants

The stability of a protein in a composition can be increased (e.g., cross-linking mediated by free —S—H moieties can be reduced) by the addition of an antioxidant, and in particular, an anti-oxidant which includes a moiety which reacts with the free —S—H (e.g., an —S—H), e.g., cysteine, cysteine-HCl, or methionine. For a protein (e.g., GCB) that contains both free thiol groups and also internal disulfide linkages within the protein molecule, the level of antioxidant (e.g., cysteine) used should be high enough to minimize cross-linking of the free thiol bonds (e.g., aggregation) but low enough so as not to cause fragmentation, and/or proteolysis, and/or degradation (e.g., detectable with reverse-phase HPLC). For example, with cysteine, particularly for GCB, inclusion of about 0.001% to about 10%, e.g., about 0.01 to about 0.15%, e.g., about 0.05% to about 0.1%, is suitable. Levels over 10% may not be optimal.

For example, one can test a candidate antioxidant (which can be any agent that can remove or reduce dissolved $O_2$ in solution) by providing a composition containing 2 mg/ml GCB, 16% sucrose (to decrease —S—H availability), adjusting the pH to 5.7, adding the candidate antioxidant (e.g., in an amount described herein, e.g., 0.075%), and purging the composition of $O_2$. The stability of the GCB composition containing the candidate antioxidant, measured, e.g., as a percent aggregation or degradation, at a predetermined time is compared with one or more standards. For example, a suitable standard would be a composition similar to the test conditions except that an antioxidant is not added to the composition. The stabilities of the treated (containing the antioxidant) and untreated (lacking an antioxidant) compositions are compared. Suitability can be shown by the test treatment increasing stability as compared with this standard. Another standard can be a composition similar to the test composition except that in place of the candidate antioxidant, an antioxidant described herein, for example, cysteine (e.g., in an amount described herein, e.g., 0.075%), is added to the composition. Suitability can be shown by the candidate antioxidant having comparable or better effects on stability than an antioxidant described herein. If the candidate antioxidant is determined to be suitable (e.g., it increases stability of the composition as compared to one of the standards), the concentration of the candidate antioxidant can be refined. For example, the concentration can be increased or decreased over a range of values and compared to the standard and to the other concentrations being tested to determine which concentration causes the greatest increase in stability.

Protein stability can be measured, e.g., by measuring protein aggregation or protein degradation. Protein aggregation can be determined, e.g., by size exclusion chromatography, non-denaturing PAGE, or other methods for determining size, etc. Protein degradation can be determined, e.g., by reverse phase HPLC, non-denaturing PAGE, ion-exchange chromatography, peptide mapping, or similar methods.

A preferred antioxidant is cysteine. Other antioxidants suitable for use include: cysteine-HCl, reduced glutathione, thioethanolamine, thiodiglycol, thioacetic acid, monothioglycerol, N-acetylcysteine, dithiothreitol, DL-thioctic acid, mercaptoethanol, dimercaptopropanol, bisulfite, dihydroacorbate, metabisulfite, sulfite, formaldehyde sulfoxylate, thiosulfate, and acetone bisulfite. In some embodiments, a combination of two or more of these antioxidants is used in the compositions described herein. The suitability of the combination can be tested as described above for a candidate antioxidant.

Addition of anti-oxidants can result in increased protein stability, e.g., by minimizing oxidation of other moieties as well, e.g., Tyr, Trp, and/or Met residues. In particular, it is desirable to minimize oxidation of these moieties in GCB.

Carbohydrates

In some embodiments, a carbohydrate is included in the composition. E.g., a carbohydrate can cause the protein to be more compact, and for example, bury or otherwise hinder access to a moiety, e.g., a cysteine residue (e.g., a free —S—H moiety on a cysteine residue), e.g., a cysteine residue in a hydrophobic domain. This can (e.g., with GCB) increase protein stability, e.g., by reducing protein aggregation.

Carbohydrates include non-reducing sugars, e.g., non-reducing disaccharides, e.g., sucrose or trehalose, which are suitable for this purpose. The level of sugar in the composition can be critical. A sugar content of about 1 to about 40%, e.g., about 5 to about 30%, e.g., about 8 to about 24%, e.g., about 16%, weight per volume (w/v) is suitable, e.g., for use with GCB. A sugar content of about 3 to about 5% is also suitable.

One can test a candidate substance, e.g., a candidate carbohydrate, for decreasing —S—H availability by providing a composition containing 2 mg/ml GCB, 0.075% cysteine (as an antioxidant), adjusting the pH to 5.7, adding the candidate substance (e.g., in an amount described herein, e.g., 16%), and purging the composition of $O_2$. The stability of the GCB composition containing the candidate substance, measured, e.g., as a percent aggregation or degradation, at a predetermined time is compared with one or more standards. For example, a suitable standard would be a composition similar to the test conditions except that a substance is not added to the composition. The stabilities of the treated (containing the substance) and untreated (lacking a substance) compositions are compared. Suitability can be shown by the test treatment increasing stability as compared with this standard. Another standard can be a composition similar to the test composition except that in place of the candidate substance, a substance described herein, for example, sucrose (e.g., in an amount described herein, e.g., 16%), is added to the composition. Suitability can be shown by the candidate substance having comparable or better effects on stability than a substance described herein. If the candidate substance is determined to be suitable (e.g., it increases stability of the composition as compared to one of the standards), the concentration of the candidate substance can be refined. For example, the concentration can be increased or decreased over a range of values and compared to the standard and to the other concentrations being tested to determine which concentration causes the greatest increase in stability.

Protein stability can be measured, e.g., by measuring protein aggregation or protein degradation. Protein aggregation can be determined, e.g., by size exclusion chromatography, non-denaturing PAGE, or other methods for determining size, etc. Protein degradation can be determined, e.g., by reverse phase HPLC, non-denaturing PAGE, ion-exchange chromatography, peptide mapping, or similar methods.

Preferred carbohydrates are trehalose or sucrose. Other preferred substances suitable for use include: maltose, raffinose, glucose, sorbitol. Other suitable substances that can be used to stabilize the protein include: carbohydrates such as lactose and arabinose; polyols such as mannitol, glycerol, and xylitol; amino acids such as glycine, arginine, lysine, histidine, alanine, methionine, and leucine; and polymers such as PEG, poloxomers, dextran, polypropylene glycol, polysaccharides, methylcellulose, sodium carboxymethyl cellulose, polyvinyl pyrrolidone (PVP), hydrolyzed gelatin, and human albumin. In some embodiments, a combination of two or more of these carbohydrates (e.g., sucrose and trehalose) is used in the compositions described herein. The suitability of the combination can be tested as described above for a candidate carbohydrate.

pH pH can be critical in achieving an optimized protein composition, e.g., a liquid protein composition with increased stability. pH can work by affecting the conformation and/or aggregation and/or degradation and/or the reactivity of the protein. For example, at a higher pH, $O_2$ can be more reactive. The pH is preferably less than 7.0, more preferably in the range of about 4.5 to about 6.5, more preferably about 5.0 to about 6.0, and more preferably about 5.5 to about 5.8, more preferably about 5.7. With some proteins, e.g., GCB, aggregation can reach undesirable levels at a pH above 7.0 and degradation (e.g., fragmentation) can reach undesirable levels at a pH under 4.5 or 5.0, or at a pH above 6.5 or 7.0.

One can test a candidate pH by providing a composition containing 2 mg/ml GCB, 0.075% cysteine (as an antioxidant), 16% sucrose (to decrease —S—H availability), adjusting the composition to a candidate pH, and purging the composition of $O_2$. The stability of the GCB composition at the candidate pH, measured, e.g., as a percent aggregation or degradation, at a predetermined time is compared with one or more standards. For example, a suitable standard would be a composition similar to the test conditions except that the pH of the composition is not adjusted. The stabilities of the treated (the composition adjusted to the candidate pH) and untreated (the pH is not adjusted) compositions are compared. Suitability can be shown by the test treatment increasing stability as compared with this standard. Another standard can be a composition similar to the test composition except that in place of the candidate pH, the composition has a pH described herein, for example, pH 5.7. Suitability can be shown by the composition at the candidate pH having comparable or better effects on stability than the composition at pH 5.7.

Protein stability can be measured, e.g., by measuring protein aggregation or protein degradation. Protein aggregation can be determined, e.g., by size exclusion chromatography, non-denaturing PAGE, or other methods for determining size, etc. Protein degradation can be determined, e.g., by reverse phase HPLC, non-denaturing PAGE, ion-exchange chromatography, peptide mapping, or similar methods.

Buffers that can be used to adjust the pH of a protein composition include: histidine, citrate, phosphate, glycine, succinate, acetate, glutamate, Tris, tartrate, aspartate, maleate, and lactate. A preferred buffer is citrate.

Protein Concentration

A preferred protein (e.g., GCB) concentration can be between about 0.1 to about 40 mg/ml, more preferably about 0.5 to about 10 mg/ml, e.g., about 2 to about 8 mg/ml or about 5 mg/ml.

One can test for a suitable protein concentration by providing a composition containing 0.075% cysteine (as an antioxidant), 16% sucrose (to decrease —S—H availability), adjusting the pH to 5.7, adjusting the protein (e.g., GCB) to a candidate concentration, and purging the composition of $O_2$. The stability of the protein (e.g., GCB) composition at the candidate concentration, measured, e.g., as a percent aggregation or degradation, at a predetermined time is compared with one or more standards. For example, a suitable standard would be a composition similar to the test conditions except that the protein (e.g., GCB) concentration is a concentration described herein, e.g., 2 mg/ml. The stabilities of the protein (e.g., GCB) at each concentration are compared. Suitability can be shown by the candidate concentration having comparable or better effects on stability than a concentration described herein.

Protein stability can be measured, e.g., by measuring protein aggregation or protein degradation. Protein aggregation can be determined, e.g., by size exclusion chromatography, non-denaturing PAGE, or other methods for determining size, etc. Protein degradation can be determined, e.g., by reverse phase HPLC, non-denaturing PAGE, ion-exchange chromatography, peptide mapping, or similar methods.

Surfactants

A surfactant can be added to the liquid protein (e.g., GCB) composition. In a preferred embodiment, this can increase protein stability, e.g., reduce protein degradation, e.g., due to air/liquid interface upon shaking/shipment. A surfactant that increases protein stability, e.g., does not cause protein degradation, in the liquid composition is selected. A surfactant suitable for use is e.g., poloxamer 188, e.g., PLURONIC® F68. The surfactant can be present in an amount between about 0.005% and about 5%, e.g., between about 0.01% and about 1%, e.g., about 0.025% and about 0.5%, e.g., about 0.03% and about 0.25%, e.g., about 0.04 to about 0.1%, e.g., about 0.05% to about 0.075%, e.g., 0.05%.

Ideally, a surfactant selected for use in the protein compositions described herein is one that is not modified, e.g., cleaved, by the protein.

For example, one can test a candidate surfactant by providing a composition containing 2 mg/ml GCB, 0.075% cysteine (as an antioxidant), 16% sucrose (to decrease —S—H availability), adjusting the pH to 5.7, adding the candidate surfactant (e.g., in an amount described herein, e.g., 0.05%), and purging the composition of $O_2$. The stability of the GCB composition containing the candidate surfactant, measured, e.g., as a percent aggregation or degradation, at a predetermined time is compared with one or more standards. For example, a suitable standard would be a composition similar to the test conditions except that a surfactant is not added to the composition. The stabilities of the treated (containing the surfactant) and untreated (lacking a surfactant) compositions are compared in conditions simulating "real world" scenarios, e.g., shipping. Suitability can be shown by the test treatment increasing stability as compared with this standard. Another standard can be a composition similar to the test composition except that in place of the candidate surfactant, a surfactant described herein, for example, poloxamer 188 (e.g., in an amount described herein, e.g., 0.05%), is added to the composition. Suitability can be shown by the candidate surfactant having comparable or better effects on stability than a surfactant described herein. If the candidate surfactant is determined to be suitable (e.g., it increases stability of the composition as compared to one of the standards), the concentration of the candidate surfactant can be refined. For example, the concentration can be increased or decreased over a range of values and compared to the standard and to the other concentrations being tested to determine which concentration causes the greatest increase in stability.

In some embodiments, a combination of two or more surfactants is used in the compositions described herein. The suitability of the combination can be tested as described above for a candidate surfactant.

Protein stability can be measured, e.g., by measuring protein aggregation or protein degradation. Protein aggregation can be determined, e.g., by size exclusion chromatography, non-denaturing PAGE, or other methods for determining size, etc. Protein degradation can be determined, e.g., by reverse phase HPLC, non-denaturing PAGE, ion-exchange chromatography, peptide mapping, or similar methods.

GCB

Gaucher disease is an autosomal recessive lysosomal storage disorder characterized by a deficiency in the lysosomal enzyme, glucocerebrosidase (GCB). GCB hydrolyzes the glycolipid glucocerebroside that is formed after degradation of glycosphingolipids in the membranes of white blood cells and red blood cells. The deficiency in this enzyme causes glucocerebroside to accumulate in large quantities in the lysosomes of phagocytic cells located in the liver, spleen, and bone marrow of Gaucher patients. Accumulation of these molecules causes a range of clinical manifestations including splenomegaly, hepatomegaly, skeletal disorder, thrombocytopenia and anemia. (Beutler et al. Gaucher disease; In: The Metabolic and Molecular Bases of Inherited Disease (McGraw-Hill, Inc, New York, 1995) pp. 2625-2639).

Treatments for patients suffering from this disease include administration of analgesics for relief of bone pain, blood and platelet transfusions and, in some cases, splenectomy. Joint replacement is sometimes necessary for patients who experience bone erosion. Enzyme replacement therapy with GCB has been used as a treatment for Gaucher disease.

The structure of GCB in solution provides relatively accessible (as opposed to buried or hindered) free —S—H moieties, which promotes reactions with the —S—H moiety.

GCB can be obtained by methods that are known in the art. For example, WO02/15927, WO2005/089047, WO03/056897, WO01/77307, WO01/07078, and WO90/07573; European Published App. No. EP1392826; U.S. Published Application Nos. 2005-0026249, 2005-0019861, 2002-0168750, 2005-0265988, 2004-0043457, 2003-0215435, and 2003-0133924; and U.S. patent application Ser. No. 10/968,870; U.S. Pat. Nos. 7,138,262, 6,451,600, 6,074,864, 5,879,680, 5,549,892, 5,236,838, and 3,910,822 describe methods or preparing GCB protein. Any of the GCB protein preparations described in these patents and applications can be formulated into a composition described herein.

GCB enzymatic activity can be measured as described in the examples provided herein, or as described in the art, e.g., in U.S. Pat. No. 7,138,262.

Packaging and Delivery

Protein compositions, e.g., GCB compositions, e.g., the compositions described herein and in WO02/15927, U.S. Published Application Nos. 2005-0026249, 2005-0019861, and 2002-0168750, and U.S. patent application Ser. Nos. 09/641,471 and 10/968,870, can be packaged in a two chamber syringe. For example, the composition in lyophilized form can be placed into a first syringe chamber and a liquid can be present in a second syringe chamber (see e.g., U.S. Published Application No. 2004-0249339).

Protein compositions, e.g., GCB compositions, e.g., the compositions described herein and in WO02/15927, U.S. Published Application Nos. 2005-0026249, 2005-0019861, and 2002-0168750, and U.S. patent application Ser. Nos. 09/641,471 and 10/968,870, can be packaged in a needleless syringe (see e.g., U.S. Pat. Nos. 6,406,455 and 6,939,324). Briefly, as one example, the injection device includes: a gas chamber containing a gas or a source of gas; a port which can allow for release of gas from the gas chamber; a plunger, which upon the release of gas from the gas chamber, can cause movement of at least a first piston; a first piston; a second piston; a first chamber, e.g. a chamber useful for drug storage and mixing; a piston housing, in which are disposed the first piston, the second piston and the first chamber; a displacement member which can, independent of the motive power of gas from the gas chamber, cause movement of one or both of the first and second pistons (the displacement member can be the plunger or a separate member); an orifice suitable for needleless injection in communication with the first chamber; wherein the first and second piston, are slideably disposed within the piston housing, and the displacement member, the source of gas, and the plunger are disposed such that: in a first position of the pistons, a second chamber, e.g., a fluid reservoir, is defined within the piston housing by the first piston, the piston housing and the second piston, the displacement member can move one or both of the pistons into a second position wherein the first piston is in a position such that the second chamber, which can be a fluid reservoir, is in communication with the first chamber, which can be a drug storage and mixing chamber, and the second piston is moved in the direction of the first piston, thereby decreasing the volume of the second chamber and allowing the transfer of fluid from the second chamber to the first chamber, the plunger, upon release of gas from the gas chamber, causes the first piston to move so as to decrease the volume of the first chamber allowing a substance to be expelled through the orifice and from the chamber and, e.g., to a subject.

The needleless syringe can include separate modules for a first component, e.g., a dry or liquid component, and a second component, e.g., a liquid component. The modules can be provided as two separate components and assembled, e.g., by the subject who will administer the component to himself or herself, or by another person, e.g., by an individual who provides or delivers health care. Together, the modules can form all or part of the piston housing of devices described herein. The devices can be used to provide any first and second component where it is desirable to store or provide the components separately and combine them prior to administration to a subject.

Protein (e.g., GCB) compositions described herein can be incorporated into pharmaceutical compositions suitable for administration to a subject, e.g., a human. A GCB composition can include a sufficient dosage of GCB to treat a subject having Gaucher disease. The pharmaceutical compositions can include one or more pharmaceutically acceptable carriers. As used herein the language "pharmaceutically acceptable carrier" is intended to include any and all solvents, excipients, dispersion media, coatings, antibacterial and antifungal agents, isotonic and adsorption delaying agents, and the like, compatible with pharmaceutical administration. Pharmaceutical formulation is a well-established art, and is further described, e.g., in Gennaro (ed.), Remington: The Science and Practice of Pharmacy, 20th ed., Lippincott, Williams & Wilkins (2000) (ISBN: 0683306472); Ansel et al., Pharmaceutical Dosage Forms and Drug Delivery Systems, 7th Ed., Lippincott Williams & Wilkins Publishers (1999) (ISBN: 0683305727); and Kibbe (ed.), Handbook of Pharmaceutical Excipients American Pharmaceutical Association, 3rd ed. (2000) (ISBN: 091733096X). Except insofar as any conventional media or agent is incompatible with the active compound, such media can be used in the compositions of the invention. Supplementary active compounds can also be incorporated into the compositions.

A pharmaceutical composition may include a "therapeutically effective amount" of a composition described herein. Such effective amounts can be determined based on the effect of the administered composition. A therapeutically effective amount of a composition may also vary according to factors such as the disease state, age, sex, and weight of the individual, and the ability of the composition to elicit a desired response in the individual, e.g., amelioration of at least one symptom of a condition or disorder, e.g., a glucocerebrosidase deficiency, e.g., Gaucher disease. A therapeutically effective amount is also one in which any toxic or detrimental effects of the composition are outweighed by the therapeutically beneficial effects.

A pharmaceutical composition of the invention is formulated to be compatible with its intended route of administration. For example, the composition can be administered by a parenteral mode (e.g., intravenous, subcutaneous, intraperitoneal, or intramuscular injection). The phrases "parenteral administration" and "administered parenterally" as used herein mean modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural, and intrasternal injection and infusion. Preferably, the route of administration is intravenous. Solutions or suspensions used for parenteral application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders, e.g., lyophilized preparations, for the extemporaneous preparation of sterile injectable solutions or dispersion. For intravenous administration, suitable carriers include physiological saline, bacteriostatic water, CREMOPHOR EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged stability of the injectable compositions can be brought about by including in the composition an agent which delays adsorption, for example, aluminum monostearate, human serum albumin and gelatin.

Sterile injectable solutions can be prepared by incorporating GCB compositions described herein in the required amount in an appropriate solvent with one or a combination of ingredients enumerated above, as required, followed by filter sterilization. Generally, dispersions are prepared by incorporating the active compound into a sterile vehicle which contains a basic dispersion medium and the required other ingredients from those enumerated above. In the case of sterile powders for the composition of sterile injectable solutions, the preferred methods of composition are vacuum drying and freeze-drying, e.g., lyophilization, which yields a powder of the active ingredient plus any additional desired ingredient from a previously sterile-filtered solution thereof.

The active compounds (e.g., GCB compositions described herein) can be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Protein compositions, e.g., GCB compositions, described herein can be administered with medical devices known in the art. For example, a protein (e.g., GCB) composition described herein can be administered with a needle-less hypodermic injection device, such as the devices disclosed in U.S. Pat. Nos. 5,399,163, 5,383,851, 5,312,335, 5,064,413, 4,941,880, 4,790,824, or 4,596,556. Examples of well-known implants and modules useful in the invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Of course, many other such implants, delivery systems, and modules also are known.

EXAMPLES

Example 1

Materials and Equipment

The following reagents were used in generating the results presented in Examples 2-6:
  GCB: Glucocerebrosidase was prepared using, but not limited to, the methods described in International App. No. PCT/US01/25882. Other methods known to one of ordinary skill in the art using recombinant DNA technology may also be used, for example, the methods described in International App. Nos. PCT/US88/04314, PCT/US89/05801, and PCT/US92/00431, and U.S. Pat. Nos. 5,236,838B1, 5,641,670B1, 5,549,892B1, and 6,270,989B1.
  Sucrose: P/N S-124-01 or S-124-02, Pfanstiehl (Waukegen, Ill.)
  Cysteine HCl: P/N 2071-05, JTBaker (Phillipsburg, N.J.)
  Poloxamer 188: P/N P1169, Spectrum (New Brunswick, N.J.)
  Sodium Citrate: P/N 3649-01, JTBaker (Phillipsburg, N.J.)
  20 mL vials: P/N 6800-0321, West Pharmaceuticals Services (Lionville, Pa.)
  2 mL vials: P/N 6800-0314, West Pharmaceuticals Services (Lionville, Pa.)
  20 mm stoppers: P/N 1950-0414, West Pharmaceuticals Services (Lionville, Pa.)
  13 mm stoppers: P/N 1950-0412, West Pharmaceuticals Services (Lionville, Pa.)
  $N_2$ gas: P/N UN1066, Airgas (Salem, N.H.)
  Lyophilizer: Genesis 35EL, SP Industries (Warminster, Pa.)

Example 2

GCB Stability

GCB was formulated at 2.5 mg/mL in 16% sucrose, 0.03% Cysteine HCl, 0.05% poloxamer 188, 50 mM sodium citrate, pH 6.0. Twenty-mL glass vials were filled at 4.5 mL each with the formulated solutions. The filled vials were loaded onto a shelf of a lyophilizer and vacuum degassed at 500 mT with a shelf temperature of 20° C. for 3 minutes, followed by backfill with $N_2$ to 950 mBar and immediately stoppered with 20 mm gray stoppers. The samples were placed into a 2-8° C. stability chamber. At 0, 6, 12, 18, and 24 months after storage, the samples were pulled and tested for enzyme activity, aggregation by SE-HPLC, and degradation changes by RP-HPLC. Enzyme activity was assayed by a colorimetric assay using p-nitrophenyl β-D-glucopyranoside as the substrate (the activity can also be assayed, e.g, using the assay described in U.S. Pat. No. 7,138,262).

The results are summarized in Table 1. GCB from this composition had less than 5% changes compared to the baseline after 24 months at 2-8° C.

TABLE 1

Stability Summary for Example 2 after 24 Months Storage at 2-8° C.

| Time point (months) | Activity* | SE-HPLC* | RP-HPLC* |
|---|---|---|---|
| 0 | 100% | 100% | 100% |
| 6 | N/A | 100% | 100% |
| 12 | 100% | 100% | 99% |
| 18 | 96% | 99% | 97% |
| 24 | 95% | 99% | 96% |

*Percentage retained from the baseline.

Example 3

Effect of $O_2$ Levels

GCB was formulated at 2.5 mg/mL GCB in 16% sucrose, 0.03% Cysteine HCl, 0.05% poloxamer 188, 50 mM sodium citrate, pH 6.0. Two-mL glass vials were filled to 1 mL each with the formulated solutions. The headspace of the vials was treated using a lyophilizer to have $O_2$ level of 3%, 6%, or 14%. The samples were placed into a 2-8° C. stability chamber. At the 6 months time point, the samples were pulled and tested for aggregation change by SE-HPLC and degradation change by RP-HPLC. The results are summarized in Table 2. GCB from these compositions is sensitive to the oxygen level in the headspace of the vial. With $O_2$ less than 3%, essentially no changes were observed after 6 months at 2-8° C.

TABLE 2

Stability Summary for Example 3 after 6 Months Storage at 2-8° C.

| O2 level in the headspace | SE-HPLC* | RP-HPLC* |
|---|---|---|
| 3% | 100% | 99% |
| 6% | 93% | 89% |
| 14% | 64% | 72% |

*Percentage retained from the baseline.

Example 4

Effect of Sucrose Levels

GCB was formulated at 2.5 mg/mL GCB in 0.05% Cysteine HCl, 0.05% poloxamer 188, 50 mM sodium citrate, pH 6.0, containing sucrose levels of 0%, 5%, 8%, or 16%. Two-mL glass vials were filled to 1 mL each with the formulated solutions. The vials were vacuum degassed by a lyophilizer and overlaid with $N_2$ to 950 mBar, followed by closing with 13 mm stoppers. The samples were placed into a 2-8° C. stability chamber. At the 6 month time point, the samples were pulled for testing of aggregation change by SE-HPLC and degradation change by RP-HPLC. The results are summarized in Table 3.

TABLE 3

Stability Summary for Example 4 after 6 Months Storage at 2-8° C.

| Sucrose level | SE-HPLC* | RP-HPLC* |
|---|---|---|
| 0% | 99.1% | 98.9% |
| 5% | 99.5% | 98.9% |
| 8% | 99.6% | 98.9% |
| 16% | 99.8% | 98.6% |

*Percentage retained from the baseline.

Example 5

Effect of Cysteine Levels

GCB was formulated at 2.5 mg/mL GCB in 16% sucrose, 0.05% poloxamer 188, 50 mM sodium citrate, pH 6.0, containing cysteine HCL of 0% or 0.05%. Two-mL glass vials were filled to 1 mL each with the formulated solutions. The vials were vacuum degassed by a lyophilizer and overlaid with $N_2$ to 950 mBar in the headspace, followed by closing with 13 mm stoppers. These samples were placed into a 2-8° C. stability chamber. At the 6 month time point, the samples were pulled for testing of aggregation change by SE-HPLC and degradation change by RP-HPLC. The results are summarized in Table 4. Addition of cysteine HCL reduced the aggregation level but increased the degradation level as detected by RP-HPLC.

TABLE 4

Stability Summary for Example 5 after 6 Months Storage at 2-8° C.

| Cysteine HCL level | SE-HPLC* | RP-HPLC* |
|---|---|---|
| 0% | 99.4% | 99.2% |
| 0.05% | 99.8% | 98.6% |

*Percentage retained from the baseline.

Example 6

Effect of pH Levels

GCB was formulated at 2.5 mg/mL GCB in 16% sucrose, 0.05% cysteine HCl, 0.05% poloxamer 188, 50 mM sodium citrate with pH of 6.0, 5.8 or 5.5. Two-mL glass vials were filled to 1 mL each with the formulated solutions. The vials were vacuum degassed and overlaid with $N_2$ to 950 mBar in the headspace, followed by closing with 13 mm stoppers. These samples were placed into a 13-17° C. stability chamber. At the 3 month time point, the samples were pulled for testing of aggregation change by SE-HPLC and degradation change by RP-HPLC. The results are summarized in Table 5. Decreasing pH can reduce both the aggregation level and the degradation level.

TABLE 5

Stability Summary for Example 6 after 3 Months Storage at 13-17° C.

| pH | SE-HPLC* | RP-HPLC* |
|---|---|---|
| 6.0 | 99.8% | 96.9% |
| 5.8 | 100% | 97.9% |
| 5.5 | 100% | 98.5% |

*Percentage retained from the baseline.

Other Embodiments

It is to be understood that while the invention has been described in conjunction with the detailed description thereof, the foregoing description is intended to illustrate and not limit the scope of the appended claims. Other aspects, advantages, and modifications are within the scope of the following claims.

What is claimed is:

1. A method of treating a subject having a glucocerebrosidase deficiency, the method comprising administering to the subject a composition comprising glucocerebrosidase (GCB) and a carbohydrate, wherein the carbohydrate is present in an amount sufficient to maintain the stability of the GCB, wherein the pH of the composition is less than 7.0, and wherein the carbohydrate is sucrose or trehalose.

2. The method of claim 1, wherein the composition is produced by a method comprising providing a GCB preparation and formulating the GCB with the carbohydrate.

3. The method of claim 2, wherein the method for producing the composition further comprises physical removal of $O_2$ from the composition.

4. The method of claim 2, wherein the method for producing the composition further comprises exposing the composition to an inert gas, wherein the inert gas is present in a concentration higher than in the ambient atmosphere.

5. The method of claim 2, wherein the method for producing the composition further comprises packaging the composition.

6. The method of claim 5, wherein the packaging comprises contacting the GCB with an inert gas to reduce the amount of a reactive species, and introducing the GCB, the inert gas, and the carbohydrate into a gas tight container.

7. The method of claim 6, wherein the container comprises a headspace comprising at least 90% (vol/vol) an inert gas.

8. The method of claim 7, wherein the container is a prefilled syringe, a vial, or ampoule.

9. The method of claim 8, wherein the prefilled syringe is a needleless syringe.

10. The method of claim 6, wherein the inert gas is $N_2$ or Ar and the reactive species is $O_2$.

11. The method of claim 1, wherein the stability is at least 5-80% greater, under pre-selected conditions, than the stability of a composition which differs by lacking the carbohydrate.

12. The method of claim 1, wherein the carbohydrate is present in an amount sufficient to increase the stability of the GCB.

13. The method of claim 1, wherein the carbohydrate is present in an amount sufficient to inhibit the reaction of a free thiol on a first molecule of the GCB with a free thiol on a second molecule of the GCB to form an aggregate.

14. The method of claim 1, wherein the carbohydrate is present in an amount sufficient to inhibit the formation of an aggregate formed by the reaction of a free thiol on a first molecule of the GCB with a free thiol on a second molecule of the GCB by at least 5- 80%, under pre-selected conditions, as compared to the same composition lacking the carbohydrate.

15. The method of claim 1, wherein the carbohydrate is present in an amount sufficient that upon storage, in a gas tight container, at a temperature of 2-8° C., for a period of 6 months, the composition will retain at least 85% of the stability the composition had prior to storage.

16. The method of claim 15, wherein the storage occurs in darkness.

17. The method of claim 1, wherein the carbohydrate is present in an amount sufficient to have stability comparable to that of a lyophilized composition comprising sucrose, 0.01% polysorbate-20, pH 6.0, 50 mM Citrate.

18. The method of claim 1, wherein the carbohydrate is present in an amount sufficient to maintain biochemical integrity and bioactivity characteristics of the GCB.

19. The method of claim 1, wherein the pH of the composition is between about 4.5 and about 6.5.

20. The method of claim 1, wherein the composition further comprises an antioxidant, wherein the antioxidant and the carbohydrate are present in amounts sufficient to maintain the stability of the GCB.

21. The method of claim 20, wherein the antioxidant is cysteine, cysteine-HCl, or methionine.

22. The method of claim 20, wherein the antioxidant is present at between about 0.001 and about 10% (wt/vol).

23. The method of claim 1, wherein the composition further comprises a surfactant.

24. The method of claim 23, wherein the surfactant is poloxamer 188.

25. The method of claim 1, wherein the composition contains less than about 10% $O_2$.

26. The method of claim 1, wherein the GCB has two, three, or more free thiol groups and has zero, two, four, or more thiol groups which form sulfhydryl bridges, per active unit of GCB.

27. The method of claim 1, wherein the composition is a liquid.

28. The method of claim 1, wherein carbohydrate is present at between about 1 and about 40% (wt/vol).

29. The method of claim 1, wherein the composition comprises about 0.1-40 mg/ml GCB, about 0.001-10% cysteine, about 1-40% sucrose, at a pH of about 5.5-6.0, and wherein the level of dissolved $O_2$ is less than about 10%.

30. The method of claim 1, wherein the composition does not comprise polysorbate.

31. The method of claim 1, wherein the glucocerebrosidase deficiency is Gaucher disease.

* * * * *